United States Patent
Caro et al.

[11] Patent Number: 5,997,516
[45] Date of Patent: Dec. 7, 1999

[54] MODIFIED CANNULA

[75] Inventors: Colin Caro; Denis Doorly, both of London, United Kingdom

[73] Assignee: Imperial College of Science, Technology & Medicine, London, United Kingdom

[21] Appl. No.: 08/849,823

[22] PCT Filed: Dec. 18, 1995

[86] PCT No.: PCT/GB95/02959

§ 371 Date: Jun. 13, 1997

§ 102(e) Date: Jun. 13, 1997

[87] PCT Pub. No.: WO96/18428

PCT Pub. Date: Jun. 20, 1996

[30] Foreign Application Priority Data

Dec. 16, 1994 [GB] United Kingdom .................. 9425493

[51] Int. Cl.⁶ ..................................................... A61M 5/00
[52] U.S. Cl. ........................................... 604/264; 604/507
[58] Field of Search ...................................... 604/264, 266, 604/268, 272, 275, 246, 360, 507; D24/112, 130; 138/40, 42, 43, 44–46; 137/808

[56] References Cited

U.S. PATENT DOCUMENTS

| | | | |
|---|---|---|---|
| 3,664,638 | 5/1972 | Grout et al. | |
| 4,182,385 | 1/1980 | Williamson | 141/65 |
| 4,284,105 | 8/1981 | Moket et al. | 138/42 |
| 4,474,206 | 10/1984 | Cannon | 137/486 |
| 4,522,504 | 6/1985 | Greverath | 366/339 |
| 4,634,434 | 1/1987 | Marino, Jr. et al. | 604/264 |
| 4,643,712 | 2/1987 | Kulik et al. | 604/4 |
| 4,801,297 | 1/1989 | Mueller | 604/280 |
| 4,850,336 | 7/1989 | Hagan | 126/307 |
| 5,174,162 | 12/1992 | Miyake et al. | 73/864.21 |
| 5,265,606 | 11/1993 | Kujawski | 128/632 |
| 5,354,288 | 10/1994 | Cosgrove et al. | 604/264 |

*Primary Examiner*—Wynn Wood Coggins
*Assistant Examiner*—Sharon E Finkel
*Attorney, Agent, or Firm*—Fay, Sharpe, Fagan, Minnich & McKee, LLP

[57] ABSTRACT

A surgical cannula includes a generally hollow inlet portion which can receive a fluid flow and an angled outlet portion connected in fluid communication with the inlet portion. The outlet portion is disposed at an angle of less than 180 degrees with respect to the longitudinal axis of the inlet portion. The inlet portion is provided with a structure to impart a rotational component of flow to fluid before such fluid encounters the angled outlet portion.

12 Claims, 4 Drawing Sheets

FLOW MEASUREMENTS

ADDITIONAL NON-PLANAR 'GOOSE-NECK' BEND

WINDOW

ADDITIONAL NON-PLANAR 'GOOSE NECK' BEND

FIG. 4(C) RUN No.1(4,2,5) Q = 4.5 l/MIN
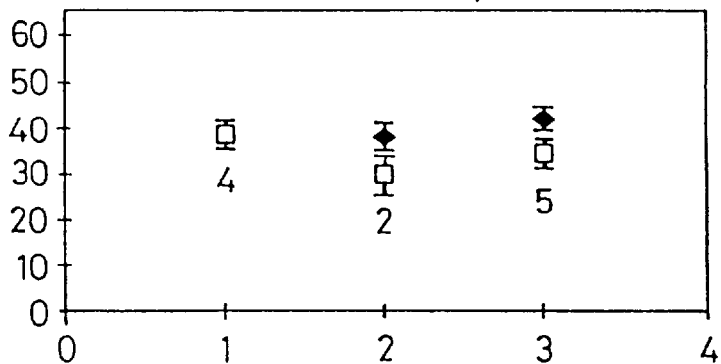
SERIES 1 = PLANAR
SERIES 2 = NON-PLANAR
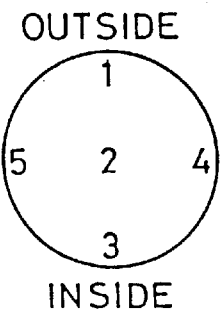
FIG. 4(D) RUN No.2(4,2,5) Q = 6 l/MIN
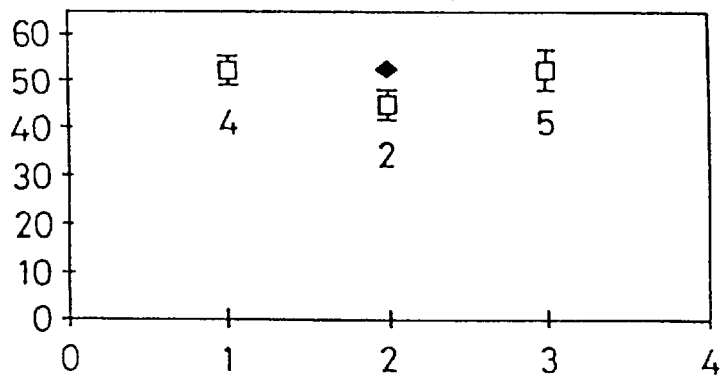
SERIES 1 = PLANAR
SERIES 2 = NON-PLANAR
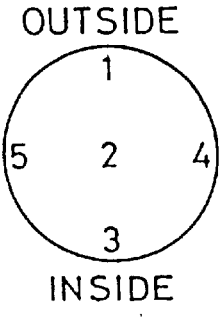

MODIFIED CANNULA

BACKGROUND OF THE INVENTION

This invention is concerned with a modified cannula and is especially applicable to cannulae adapted for use in connecting a heart lung machine to a patient's aorta during open-heart surgery.

Cannulae are devices which connect items of hardware or drainage vessels to a patient's body. During heart surgery, for example, a patient's blood is oxygenated and circulated by an artificial heart lung machine. A surgical incision is made into the patient's aorta wherein a cannula is surgically secured such that the outlet end is directed into and along the route of the aorta.

The present invention finds application with cannulae generally, but specifically it is well suited to the modification of cannulae adapted to supply blood from a heart lung machine.

With conventional such cannulae there have been flow problems associated with the relatively high velocity of blood into the aorta. There are also concerns over the possible dislodgement of fatty tissue from the vicinity of the aorta and its potentially serious implications.

Problems can arise during aortic perfusion associated with cardiopulmonary bypass surgery. Specifically, there is concern that blood emerging at high velocity from cannulae could damage the aortic wall and/or dislodge atheromatous plaque and hence cause embolic phenomena. A secondary concern is that high velocities (and related high impact pressures) might disturb the distribution of flow to the great vessels originating from the arch.

For cannula of the heart lung machine type, there is sometimes a bend in the tubing for the surgeon's convenience whilst simultaneously permitting flow of blood along the general route of the aorta. Commercially produced cannulae, e.g. of the type 3M Sarns Healthcare 'soft flow' and 'D4' cannulae, incorporate such a planar bend.

A feature of both Soft Flow and D4 cannulae is a sharp planar bend near the tip. It has been found that such a bend causes skewing of the velocity profile, with high velocities at the outer wall of curvature and low velocities (and possibly flow separation and flow reversal) at the inner wall of curvature.

Accordingly, it has been considered desirable to develop a new and improved cannula which would overcome the foregoing difficulties and others while providing better and more advantageous overall results.

SUMMARY OF THE INVENTION

In an effort to reduce the flow velocity of blood which exits from the cannula and minimise the force of impact on and around the internal surfaces of the aorta, the profile of the outlet of the cannula has been subjected to various modifications. One of these modifications is shown in FIG. 2 herein.

A consideration of the conventional design of cannulae for heart lung machines and their shortcomings has led to the development of the present invention. It has surprisingly been found that modification of the flow velocity profile in a particular way before the flow encounters the bend, reduces the severity of the impact forces on the interior of the aorta wall and helps to alleviate other difficulties associated with the design of conventional such cannulae.

Accordingly, the inventors proposed that, if there was to be modification of the cannulae with preservation of the bend, the flow should be made non-planar in type. Non-planar-type flow has been found to be characterised by swirling predominantly in one sense, strong mixing, and a relatively uniform distribution circumferentially of near-wall velocity. As a means of achieving such a flow, a twisted strip can be introduced into the cannulae, immediately upstream of the planar bend, the strip having a helical twist. Alternatively (or additionally) a swirling flow can be provided both in 'soft flow' and 'D4' cannulae by rendering the curvature non-planar e.g. introduce a bend in a plane different from the plane of the existing bend.

According to this invention we provide a surgical cannula comprising a generally hollow inlet portion which can receive a fluid flow and an angled outlet portion connected in fluid communication with said inlet portion, and said outlet portion disposed at an angle of less than 180° with respect to the longitudinal axis of said inlet portion, characterised in that the inlet portion is provided with means to impart a rotational component of flow to fluid before such fluid encounters said angled outlet portion.

The means to impart a rotational component may be internally located e.g. within the inlet portion and may further be in contact with the flow of fluid in use. Alternatively such means could be externally located, providing or causing a tangential flow of fluid. Such means could be provided by forming a spiral twist in the body of the inlet portion.

BRIEF DESCRIPTION OF THE DRAWINGS

In order that the invention may be illustrated, more easily appreciated and readily carried into effect by one skilled in the art, embodiments of modified cannulae will now be described purely by way of non limiting example only with reference to the accompanying drawings wherein.

DETAILED DESCRIPTION OF THE PREFERRED EMBODIMENT

Figure 1:
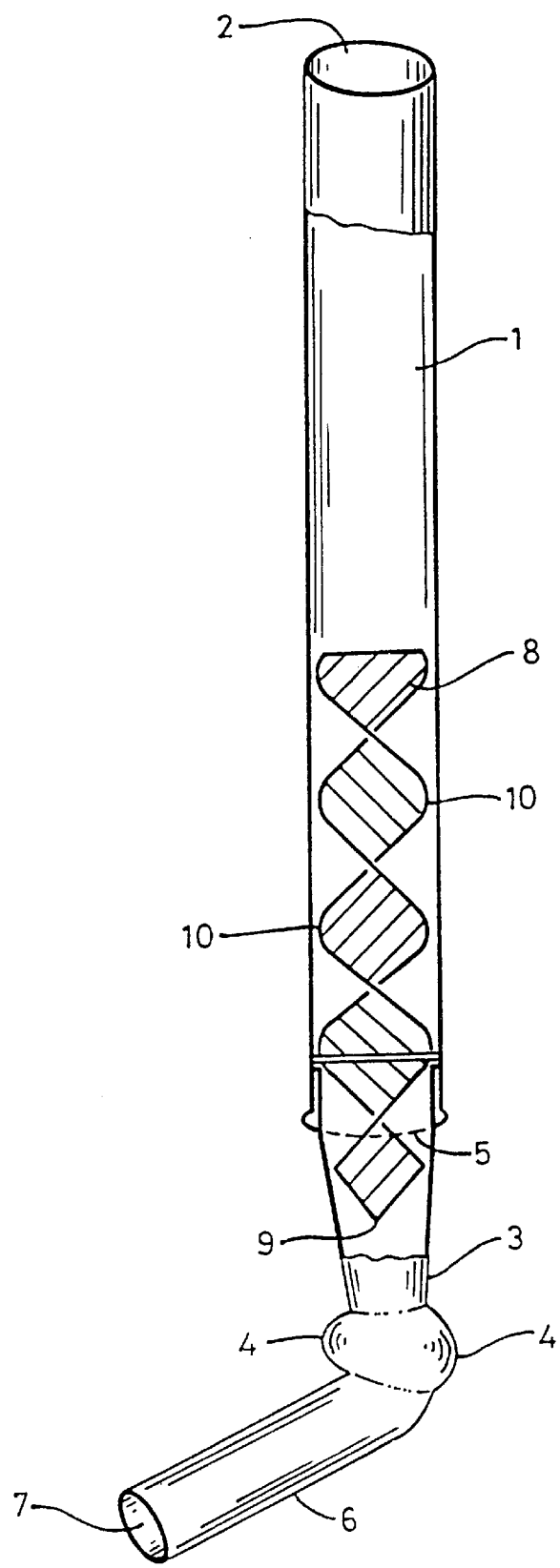
FIG. 1 is an isometric view of a modified cannula.

Referring initially to FIG. 1, a cannula of the type used for connecting a heart lung machine to a patient's aorta is shown. A flexible tubular inlet portion 1 has a hollow interior section 2 and is securely affixed by heat welding or adhesive to a more rigid outlet portion 3, 4, 6 which is also hollow and generally tubular but with a slight taper towards the outlet end 7 of the said portion 6. A hollow lumen extends between the inlet portion 1 and the outlet portion 3, 4, 6 of the cannula. The end 5 of tube 1 overlaps part 3 of the outlet portion although other arrangements are possible. There is a bulbous kink 4 provided to form an abutment over which the surgical incision in the aorta can be repaired and fastened, to prevent unintentional withdrawal of the cannula in use. The outlet section 6 of the portion is angled at approximately 120° with respect to the longitudinal axis of the inlet 1, providing planar curvature in the structure.

In use, the inlet 1 is fastened to the blood supply line from a heart lung machine (not shown) whereupon oxygenated blood is fed into the aorta through the hollow interior of the inlet and outlet portions. In doing so, the blood is forced at relatively high flow rates, to undergo a change in direction at the planar curvature which forms a 'bend' in the region of the bulbous projection 4 between the parts 3 and 6 of the outlet portion.

It has been found that the bend can interfere with the flow of blood causing it to impact upon the tissue within the aorta. There may be an increased tendency to propagate clots in the region of the bend. The present inventors have modified the cannula, in one embodiment of the present invention, by providing means internally of the cannula and 'upstream' of the 'bend' which causes a velocity shift to the flow of blood by introducing a rotational component to the flow. In one embodiment of such means, as illustrated in FIG. 1, an insert of spirally twisted or otherwise helically wound material 8 is located inside the inlet portion, upstream of the angled outlet section 6. Ideally such material should have at least two full 'twists' 10 whereby the flow is caused to rotate at least once through 180° more preferably 270° and even more preferably through 360° or more during its linear travel.

The end 9 of the insert 8 may be linear, curved or pointed. It can be of suitable biocompatible materials e.g. plastics or metal known or shown to induce no undesirable effects on the blood flowing over it. For example it might be constructed from high density polyethylene, polypropylene or stainless steel.

After flow of blood along the inlet 1 and past the insert 8, the flow will have become 'twirl' or 'swirl' flow and the severity of impact on exit from the discharge end of the outlet section 6 will have been reduced, with improved flow in the internal region of the bend at the bulbous projection 4.

Figure 2:
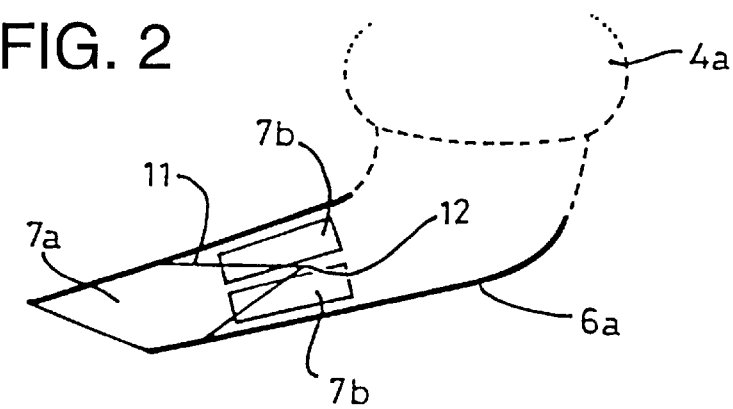
FIG. 2 is a section of an outlet end of a conventional cannula which may also be modified according to the present invention.
Figure 3A:
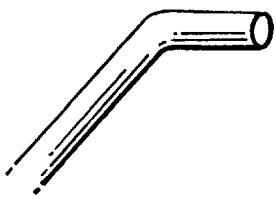
FIG. 3a shows a cannula before modification.
Figure 3B:
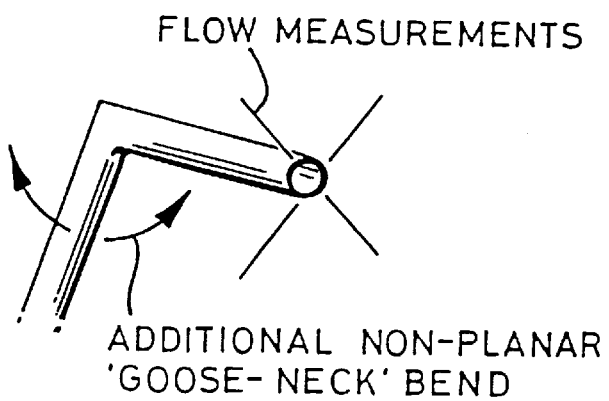
FIG. 3b shows a cannula with compound, non-planar bends illustrated schematically, and showing the points of flow measurement.
Figure 3C:
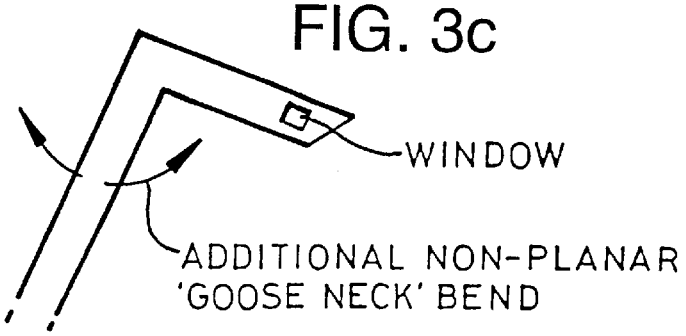
FIG. 3c is a similar view of a SARNS 3M cannula incorporating the 'window' arrangement of FIG. 2 and the non-planar curvature by means of an additional 'gooseneck'
Figure 4A:
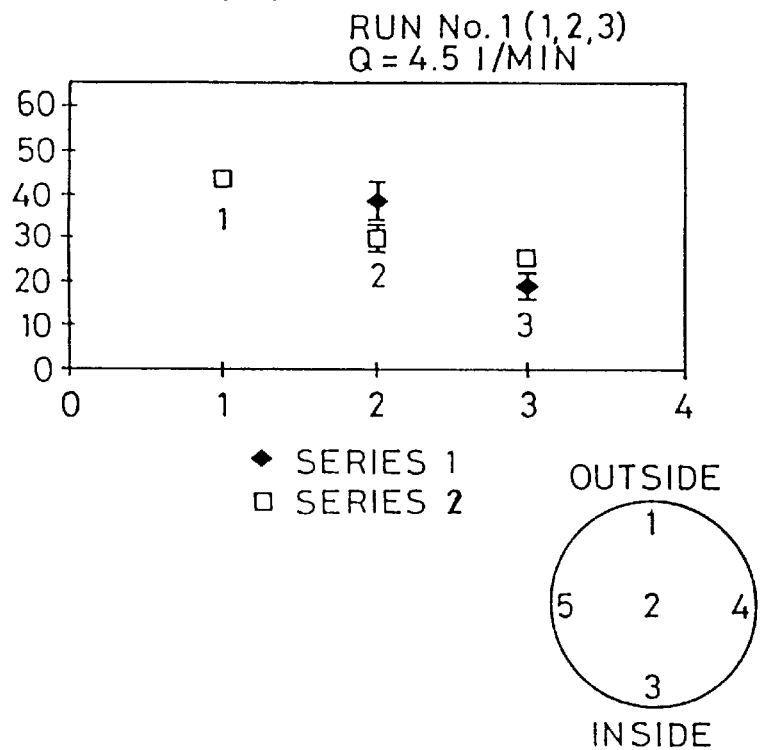
FIG. 4 shows velocity profiles in a SARNS D4 cannula at exit points 1–5 as shown using conventional planar geometry for the bend, compared with the modified non-planar geometry according to the invention.
Figure 4B:
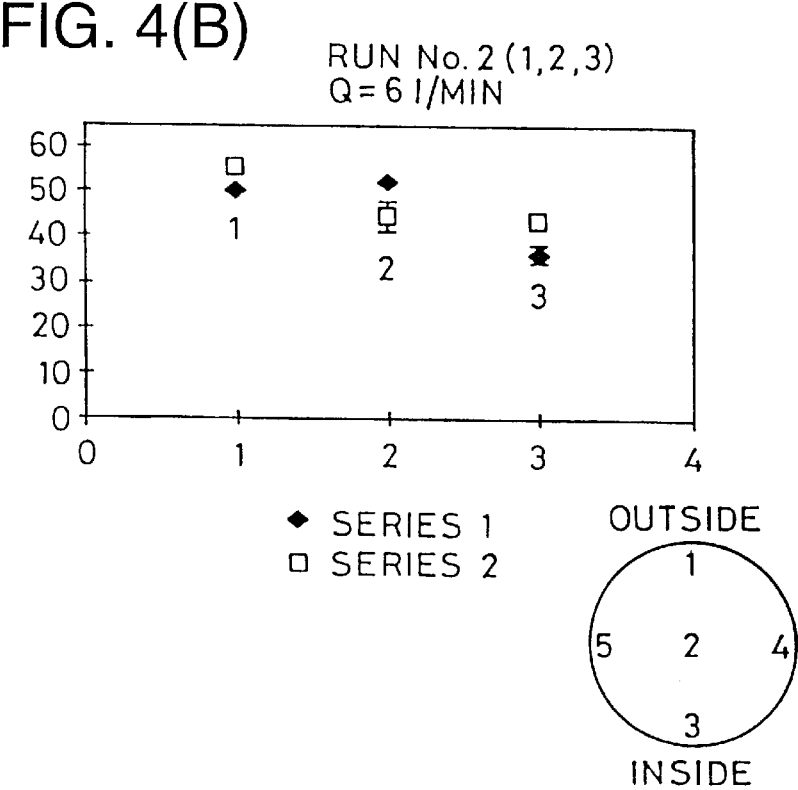

In place of the outlet section 6 shown in FIG. 1, the embodiment may be modified by using the outlet section shown in FIG. 2. This section shows an arrangement previously devised to reduce the severity of the impact of blood flowing from the outlet end of a fairly high pressure, high flow rate pump. The present invention is amenable to use in such cannulae as are also shown in FIG. 2. The bulbous formation 4a is an integral part of the outlet section 6a with a 'closed' end 7a and an internal conical projection 11 with apex 12 and a series of four (only two of which are shown) discharge orifices 7b in the region of said internal conical projection.

Other designs of outlet section will be possible since the invention is essentially concerned with modifying the velocity profile of the rapidly flowing blood before it encounters the planar curvature i.e. before being forced to turn by the angled section of the outlet portion.

As foreshadowed earlier, some device might be fastened externally of the inlet 1 to confer a tangential flow, or the tubing forming the inlet could be at least partially twisted in the form of a spiral helix over part of its length before the planar curvature of the bend.

The specific embodiments compare the results obtained with an unmodified Soft Flow cannula with those obtained following the introduction of a twisted strip see FIG. 1. The strip was made of thin aluminium; had a length of 16 cm, a pitch of about 3 cm, and a diameter of 0.8 cm, but was tap red downstream, so that it could extend to within a short distance of the planar bend. The test fluid was water, the flow was steady at a rate of about 6 1/min, and the flow exited from the cannular into air.

With the unmodified cannular, distinct jets emerged from the two outer wall of curvature 'windows' whereas at the inner wall of curvature 'windows' they were far less distinct, merging into a sheet. Following the introduction of the twisted strip, there were distinct (and similar) jets at both the outer and inner wall of curvature 'windows'.

With the unmodified cannula, the ratio combined flow rate at the two outer wall of curvature 'windows'/combined flow rate at the two inner wall of curvature 'windows' typically took a value of 1.5. Following the introduction of the twisted strip, the ratio typically took a value of 1.1.

A Pitot tube (od 4 mm, id 3 mm) was used to obtain a crude measurement of the impact pressure of the jet issuing from an outer wall of curvature 'window'. With both the concave-recess cannula and the cone-type cannula, the relative impact pressures were about 24 units. However, the introduction of the twisted strip caused the relative impact pressures for the concave-recess cannula and the cone-type cannula to become respectively 16 and 12 units.

At the same time, studies were carried out on the effect of the twisted strip on the flow exiting from a D4 cannula. These were qualitative studies. They showed that with the unmodified (planar) cannula the diameter of the emerging jet was constant for several cm downstream, whereas with the twisted strip in place, the diameter of the jet increased in the downstream direction. Moreover, there was evidence of swirling in the jet, predominantly in one sense.

In the examples employing non-planar compound bends the same general methods have been employed as previously described. However, there has been use of a smaller Pitot tube (od 0.5 mm, id 0.3 mm) to allow measurement of impact pressure with improved spatial resolution. With Soft Flow cannulae, peak impact pressure was measured in an outer wall of curvature 'window' and an inner wall of curvature 'window' about 1 cm from the window. With D4 cannulae, impact pressure was measured in the jet about 1 cm from the cannula tip, at three stations over two orthogonal diameters.

Constancy of cannula geometry upstream of the tip improved the reproducibility of measurements. In addition, the flow became most prominently non-planar in type when the upstream bend was severe and close to the downstream bend. Therefore, a constant upstream geometry is preferred and modified cannulae have been used, which possessed the required geometric characteristics. Results obtained with a Soft Flow cannula and a D4 cannula are reported separately in tables 1 and 2 hereunder.

TABLE 1

| | Soft Flow Cannula | |
|---|---|---|
| | Planar | Non-planar |
| Flow rate | $o^a$ 3400 | $o^a$ 3300 |
| (ml/min) | $i^b$ 2300 | $i^b$ 2600 |
| | o/i 1.48 | o/i 1.27 |
| Peak impact | $o^c$ 56.5 | $o^c$ 47.9 |
| pressure | $i^d$ 35.9 | $i^d$ 43.9 |
| (cm $H_2O$) | o/i 1.57 | o/i 1.09 |
| Peak | $o^c$ 238 | $o^c$ 219 |
| calculated | $i^d$ 189 | $i^d$ 210 |

TABLE 1-continued

Soft Flow Cannula

|  | Planar | Non-planar |
|---|---|---|
| velocity (cm/s) | o/i 1.26 | o/i 1.04 |

[a] combined flow outer wall of curvature windows
[b] combined flow inner wall of curvature windows
[c] one outer wall of curvature window
[d] one inner wall of curvature window

TABLE 2

D4 Cannula

|  | Planar | Non-planar |
|---|---|---|
| Run 1 | | |
| Flow rate (ml/min) | 4.5 | 4.5 |
| Impact pressure (cm H$_2$O) | 1 42.9 (0) | 1 42.9 (1.5) |
| | 2 38.5 (3.0) | 2 29.6 (4.5) |
| | 3 19.2 (1.5) | 3 25.2 (3.0) |
| | 4 40.0 (1.5) | 4 38.5 (3.0) |
| | 5 42.2 (1.5) | 5 34.0 (3.0) |
| Run 2 | | |
| Flow rate (ml/min) | 6.0 | 6.2 |
| Impact pressure (cm H$_2$O) | 1 50.3 (0) | 1 54.8 (0) |
| | 2 51.8 (0) | 2 44.4 (3.0) |
| | 3 36.3 (1.5) | 3 42.9 (0) |
| | 4 51.8 (0) | 4 51.8 (3.0) |
| | 5 51.8 (0) | 5 51.8 (4.5) |
| Run 3 | | |
| Flow rate (ml/min) | | 6.2 |
| Impact pressure (cm H$_2$O) | | 1 53.3 (4.5) |
| | | 2 45.9 (3.0) |
| | | 3 44.4 (4.5) |
| | | 4 56.2 (1.5) |
| | | 5 59.2 (6.0) |

It may be noted that the impact pressure measurements were made symmetrically about the plane of curvature of the downstream bend. As a result, they adequately represent the velocity field for the case of non-planar geometry, because it can be expected that the secondary motion will then be rotated out of the plane of curvature of the downstream bend. It may also be noted that for a flow rate of 6 1/min and a typical cannula inner diameter of 0.7 cm, the Reynolds number was about 18,000.

Soft Flow cannula: In tests using the planar (unmodified) cannula, the ratio combined flow rates at the two outer wall of curvature 'windows'/combined flow rates at the two inner wall of curvature 'windows' took a value of about 1.5. The twisted strip caused a reduction in the value of this ratio to 1.1, whereas the introduction of non-planar geometry caused a lesser reduction, i.e. from 1.43 to 1.27. More severe curvature at the upstream bend and/or bringing of the two bends closer together, may produce a greater reduction of the value of the ratio.

The ratio peak impact pressure at outer 'window'/peak impact pressure at inner 'window' was not measured initially, but later found to take a value of about 1.6. In the initial tests the introduction of a twisted strip could halve the impact pressure at the outer 'window'. In contrast, the introduction of non-planar curvature reduced peak impact pressure at the outer 'window' by about 16%. More severe curvature at the upstream bend and/or the bringing of the two bends closer together, may produce a greater reduction of that pressure.

The ratio peak impact pressure at outer 'window'/peak impact pressure at inner 'window' took a value of about 1.6 in the planar cannula and 1.1 in the non-planar cannula. The possible clinical significance of that finding is discussed below.

D4 cannula: The introduction of the twisted strip and of non-planar curvature appeared to cause swirling predominantly in one sense in the exiting jet and expansion of the jet downstream of the exit orifice.

Impact pressures were not measured in initial tests involving the twisted strip. However, later tests showed that impact pressures were lower at the centre of the jet and the inner wall of curvature of the downstream bend, with non-planar geometry than with the unmodified (planar) cannula (see Table 2 and graphs).

Clinical significance: There have been concerns that high impact pressures could damage the aortic wall and/or dislodge atheromatous plaque and hence cause embolic phenomena. There have also been concerns that high exit velocities and high impact pressures in the aorta could disturb the distribution of flow to the great vessels originating from the arch.

The illustrated and described embodiments demonstrate that non-planar-type flow can reduce both peak exit velocities and peak impact pressures. Such flow can be generated internally within the interior of the generally hollow cannula by means of a twisted strip or by rendering cannula geometry non-planar. The latter embodiments may be preferred because of greater simplicity of construction of a device and possibly its being more robust.

Whilst complications could arise during cardiopulmonary bypass perfusion, from high velocities and high impact pressures, there may also be problems from low velocities and low impact pressures. The latter complications would be associated with low wall shear and long fluid residence times, and could include thrombosis and embolism. Therefore, cannulae which can generate a relatively uniform velocity field, such as those within the scope of the present invention could be commercially desirable.

We claim:

1. A surgical cannula comprising a generally hollow inlet portion adapted to receive a fluid flow, and an angled outlet portion connected in fluid communication with said inlet portion, and said outlet portion is disposed at an angle of less than 180° with respect to the longitudinal axis of said inlet portion, characterized in that the inlet portion is provided with means to impart a rotational component of flow to fluid before such fluid encounters said angled outlet portion, said means comprising a spirally twisted component.

2. A cannula as claimed in claim 1 wherein the means to impart the rotational component is internally located.

3. A cannula as claimed in claim 2 wherein the said means are located within the inlet.

4. A cannula as claimed in claim 1, wherein the means is in direct contact with the fluid flow in use.

5. A cannula as claimed in claim 1 wherein the component has a helical or part-helical twist along its length or over a part of its length.

6. A cannula as claimed in claim 5 wherein the outlet portion includes a conical end point and a plurality of exit windows in the region of the conical end point, through which fluid can flow.

7. A surgical cannula comprising a generally hollow inlet portion adapted to receive a fluid flow, and an angled outlet portion connected in fluid communication with said inlet portion, wherein the inlet portion includes a bend which is non-planar with respect to the outlet portion, and said outlet portion is disposed at an angle of less than 180° with respect to the longitudinal axis of said inlet portion, wherein the inlet portion is provided with means to impart a rotational component of flow to fluid before such fluid encounters said angled outlet portion.

8. A cannula as claimed in claim 7 wherein the said bend is an integral part of the cannula.

9. A surgical cannula comprising a generally hollow inlet portion adapted to receive a fluid flow, and an angled outlet portion connected in fluid communication with said inlet portion, wherein the outlet portion includes a conical end point and a plurality of exit windows in the region of the conical end point, through which fluid can flow, and said outlet portion is disposed at an angle of less than 180° with respect to the longitudinal axis of said inlet portion, characterized in that the inlet portion is provided with means to impart a rotational component of flow to fluid before such fluid encounters said angled outlet portion.

10. A surgical cannula comprising a generally hollow inlet portion adapted to receive a fluid flow, and an angled outlet portion connected in fluid communication with said inlet portion, and said outlet portion disposed at an angle of less than 180° with respect to the longitudinal axis of said inlet portion, characterized in that the inlet portion is provided with means located within the inlet portion to impart a rotational component of flow to fluid before such fluid encounters said angled outlet portion, wherein the means comprises a spirally twisted component.

11. A cannula as claimed in claim 10 wherein the component has a helical or part helical twist along its length or over a part of its length.

12. A cannula as claimed in claim 11 wherein the outlet portion includes a plurality of exit windows in the region of a conical end point, through which fluid can flow.

* * * * *